(12) United States Patent
Benson

(10) Patent No.: US 12,049,975 B2
(45) Date of Patent: *Jul. 30, 2024

(54) FLUID COUPLINGS

(71) Applicant: Colder Products Company, Roseville, MN (US)

(72) Inventor: Timothy C. Benson, Andover, MN (US)

(73) Assignee: Colder Products Company, Roseville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/116,516

(22) Filed: Mar. 2, 2023

(65) Prior Publication Data

US 2023/0220935 A1 Jul. 13, 2023

Related U.S. Application Data

(63) Continuation of application No. 17/532,197, filed on Nov. 22, 2021, now Pat. No. 11,614,192.

(60) Provisional application No. 63/146,816, filed on Feb. 8, 2021.

(51) Int. Cl.
F16L 37/30 (2006.01)

(52) U.S. Cl.
CPC .......... *F16L 37/30* (2013.01); *F16L 2201/44* (2013.01)

(58) Field of Classification Search
CPC . F16L 37/30; F16L 37/36; F16L 37/38; F16L 37/44; F16L 2201/44; A61M 39/18; A61M 39/16; A61M 39/10; A61M 39/00; A61M 2039/226; A61M 39/22; A61M 39/26; F16K 31/445

See application file for complete search history.

(56) References Cited

U.S. PATENT DOCUMENTS

| | | |
|---|---|---|
| 2,758,611 A | 8/1956 | Michaels |
| 2,898,130 A | 8/1959 | Hansen |
| 3,367,626 A | 2/1968 | Stern |
| 3,731,705 A | 5/1973 | Butler |
| 3,856,262 A | 12/1974 | Jordan |
| 3,865,411 A | 2/1975 | Rowe et al. |
| 4,384,660 A | 5/1983 | Palmisano et al. |
| 4,483,510 A | 11/1984 | Palau et al. |
| 4,767,058 A | 8/1988 | Larosa et al. |

(Continued)

FOREIGN PATENT DOCUMENTS

| | | |
|---|---|---|
| EP | 1616938 | 1/2006 |
| GB | 2246746 | 2/1990 |

(Continued)

OTHER PUBLICATIONS

International Search Report and Written Opinion in International Appln. No. PCT/US2021/60296, dated Feb. 18, 2022, 10 pages.

(Continued)

*Primary Examiner* — David Colon-Morales
(74) *Attorney, Agent, or Firm* — Fish & Richardson P.C.

(57) ABSTRACT

Fluid coupling devices can be used to provide fluid passage connections in fluid systems. Some fluid coupling devices are configured for use in fluid systems for the purpose of providing a sterile connection by which fluid can be transferred in a sterile manner. Such a sterile connection can be useful for the delivery and/or processing of therapeutic agents, or ingredients thereof, and other purposes.

20 Claims, 7 Drawing Sheets

(56) References Cited

U.S. PATENT DOCUMENTS

| | | | |
|---|---|---|---|
| 5,806,832 A | 9/1998 | Larbuisson | |
| 6,161,578 A | 12/2000 | Braun et al. | |
| 6,298,876 B1 | 10/2001 | Bogdonoff et al. | |
| 7,753,340 B2 | 7/2010 | Liepold et al. | |
| 7,927,316 B2 | 4/2011 | Proulx et al. | |
| 8,033,523 B2 | 10/2011 | King et al. | |
| 8,104,643 B2 | 1/2012 | Pruvot et al. | |
| 8,322,756 B2 | 12/2012 | Elton et al. | |
| 8,544,497 B2 | 10/2013 | Hillier et al. | |
| 8,662,108 B2 * | 3/2014 | Haunhorst | F16L 37/0841 251/248 |
| 8,720,487 B2 | 5/2014 | Cooley | |
| 8,807,525 B2 | 8/2014 | Chang | |
| 8,814,137 B2 * | 8/2014 | Wong | F16L 37/18 251/149.9 |
| 8,967,177 B2 * | 3/2015 | Haunhorst | F16L 37/36 137/614.01 |
| 9,364,653 B2 * | 6/2016 | Williams | F16L 37/30 |
| 9,416,902 B2 | 8/2016 | Von Keitz | |
| 9,726,308 B2 | 8/2017 | Williams et al. | |
| 9,770,581 B2 | 9/2017 | Gerst et al. | |
| 9,849,277 B2 | 12/2017 | Stroup | |
| 9,901,729 B2 * | 2/2018 | Vigna | A61M 39/18 |
| 10,299,993 B2 | 5/2019 | Stroup | |
| 10,471,454 B2 | 11/2019 | Goettke | |
| 10,801,655 B2 | 10/2020 | Wu | |
| 10,864,364 B2 * | 12/2020 | Mack | A61M 39/26 |
| 11,480,281 B2 | 10/2022 | Benson | |
| 11,614,192 B2 * | 3/2023 | Benson | A61M 39/18 251/148 |
| 2002/0024216 A1 | 2/2002 | Rose et al. | |
| 2002/0129858 A1 | 9/2002 | Meyer et al. | |
| 2006/0211996 A1 | 9/2006 | Trinchera et al. | |
| 2016/0186906 A1 | 6/2016 | Blake et al. | |
| 2018/0056310 A1 | 3/2018 | Dodd | |
| 2018/0296817 A1 | 10/2018 | Burdge | |
| 2020/0146934 A1 | 5/2020 | Werth et al. | |

FOREIGN PATENT DOCUMENTS

| | | |
|---|---|---|
| GB | 2246745 | 2/1992 |
| KR | 20090045112 | 5/2009 |
| WO | WO 2020/251883 | 12/2020 |

OTHER PUBLICATIONS

International Preliminary Report on Patentability in International Appln. No. PCT/US2021/06296, mailed on Aug. 17, 2023, 8 pages.

Extended European Search Report in European Appln No. 21925071.9, dated Jun. 6, 2024, 9 pages.

* cited by examiner

FLUID COUPLINGS

CROSS-REFERENCE TO RELATED APPLICATIONS

This application is a continuation application of U.S. application Ser. No. 17/532,197 filed on Nov. 22, 2021, which claims the benefit of U.S. Provisional Application Ser. No. 63/146,816, filed on Feb. 8, 2021. The disclosure of the prior applications are considered part of (and are incorporated by reference in) the disclosure of this application.

BACKGROUND

1. Technical Field

This document relates to fluid coupling devices for fluid systems and methods of using the fluid coupling devices. For example, some embodiments described in this document relate to fluid couplings that can be used to provide a sterile connection for the delivery of therapeutic agents, or ingredients thereof, and other purposes.

2. Background Information

Fluid systems commonly include components such as tubing, pumps, reservoirs, fittings, couplings, heat exchangers, sensors, filters, valves, seals, and the like. Such components can be connected together in a network to define one or more fluid flow paths. Some fluid systems are open systems, meaning that the fluid flows through the network once and then exits the network or is open to the environment. Other fluid systems are closed systems, meaning that the fluid recirculates within the network of components.

Fluids may be moved through fluid systems using fluid pressure differentials. For example, in some cases, a pump or a vacuum source is used to create a pressure differential that causes the fluid to flow within the fluid system. In another example, gravity is used to cause the fluid to flow within the fluid system. In still other examples, mechanical means can be used to exert exterior force on a tube or reservoir causing fluid to flow. A peristaltic pump is one example. In other examples, a combination of such techniques is used to cause the fluid to flow within the fluid system.

Some fluid couplings can be used for sterile fluid conveyance, such as for connecting a source of one or more sterile ingredients to a sterile processing system, such as a bioreactor or other type of sterile system or container. Fluid couplings for sterile fluid conveyance can also be used for extracting samples from a sterile processing system. Fluid couplings for sterile fluid conveyance can also be used to connect together two or more pieces of sterile processing equipment.

SUMMARY

This document describes fluid coupling devices for fluid systems and methods of using the fluid coupling devices. For example, some embodiments described in this document are fluid couplings that can be used to provide a sterile connection for the delivery of therapeutic agents, or ingredients thereof, and other purposes.

In one aspect, this disclosure is directed to a fluid coupling device that includes a housing defining an internal space and a longitudinal central axis, a valve member disposed within the internal space, and a sleeve removably coupled to the housing and including one or more projections extending through one or more openings defined by the housing and engaging the valve member to thereby retain the valve member in a first position within the internal space.

Such a fluid coupling may optionally include one or more of the following features. The first position may be a closed position that blocks fluid flow through the fluid coupling device. The first position may be an open position that allows fluid flow through the fluid coupling device. The sleeve may be configured to be uncoupled from the housing such that the one or more projections disengage from the valve member. The first position may be a closed position that blocks fluid flow through the fluid coupling device. The valve member may be configured to, in response to disengagement of the one or more projections from the valve member, move from the closed position to an open position that allows fluid flow through the fluid coupling device. The fluid coupling device may also include a spring disposed within the internal space. The first position may a closed position that blocks fluid flow through the fluid coupling device, and wherein the valve member may be configured to move from the closed position to an open position that allows fluid flow through the fluid coupling device in response to: (i) the disengagement of the one or more projections from the valve member and (ii) force from the spring exerted on the valve member. The spring may be outside of a fluid flow path defined by the fluid coupling device. The fluid coupling device may also include a valve seat within the internal space. The valve seat may define a through-hole through which the longitudinal central axis extends. The valve member may abut the valve seat while the valve member is in the first position to provide a fluid seal therebetween. The fluid coupling device may also include a membrane having a portion removably attached to a front face surface of the housing and covering an end portion of a seal member that projects longitudinally beyond the front face surface. The fluid coupling device may also include a handle attached to the membrane. The handle may be releasably coupleable to the housing. In some embodiments, while the handle is coupled to the housing, the handle covers the portion of the membrane that is removably attached to the front face surface of the housing. The fluid coupling device may also include a valve seal member coupled to the valve member. The valve seal member may seal the fluid coupling device to block fluid flow through the fluid coupling device while the valve member is in the first position. In some embodiments, the sleeve has a C-shaped cross-section and surrounds the housing by greater than 180° and less than 360°. The sleeve may be configured to flex to allow removal of the sleeve from being coupled to the housing. In some embodiments, the sleeve is configured to be torn in order to remove the sleeve from being coupled to the housing. The one or more projections may consist of two projections that are arranged 180° opposite of each other on the sleeve. The fluid coupling device may also include a valve seat within the internal space and in contact with the valve member. In some cases, the valve seat is an elastomer. In other cases, the valve seat is a rigid thermoplastic or metal. In some embodiments, the valve member comprises an annular seal member or comprises an elastomeric sealing material. The fluid coupling device may also include a connection structure for non-releasably attaching the fluid coupling device to another fluid-handling component. In some embodiments, the fluid coupling device is a genderless device that is configured to non-releasably couple with a second fluid coupling device that is identical to the fluid coupling device.

In another aspect, this disclosure is directed to a method of coupling a fluid coupling device to a second fluid-handling component to create an aseptic fluid flow path between them. The method includes: (i) providing the fluid coupling device comprising a housing defining an internal space and a longitudinal central axis, a valve member disposed within the internal space, and a sleeve removably coupled to the housing and including one or more projections extending through one or more openings defined by the housing and engaging the valve member to thereby retain the valve member in a closed position within the internal space; (ii) coupling the fluid coupling device to the second fluid-handling component; (iii) after the coupling, removing one or more membranes from between the fluid coupling device and the second fluid-handling component; (iv) after the removing one or more membranes, removing the sleeve from the housing. The valve member may move from the closed position to an open position in response to the removing the sleeve.

Particular embodiments of the subject matter described in this document can be implemented to realize one or more of the following advantages. First, in some embodiments, the fluid coupling devices can be configured as "sterile" or "aseptic" coupling devices in that the fluid coupling devices can be coupled to another fluid-handling component in a manner that establishes a sterile fluid flow path between them. Such an "aseptic" coupling will also serve to limit the exposure of the fluid to the surrounding environment.

Second, in some embodiments the fluid coupling devices provided herein are configured to provide a normally closed fluid flow path. In use, the fluid coupling devices can be coupled to another fluid-handling component while the fluid flow path of the fluid coupling device is maintained in the closed configuration. Thereafter, the user of the fluid coupling devices can selectively open the fluid flow path at a desired time or process step.

Third, in some embodiments the fluid flow path of the fluid coupling devices described herein can be selectively opened by easily removing a sleeve from the main body of the fluid coupling device. The removal of the sleeve releases a valve member such that the valve member reconfigures from its closed position to an open position in which the fluid flow path is open through the fluid coupling device.

Fourth, some embodiments of the fluid coupling devices provided herein are genderless couplings, meaning that a pair of two single couplings that are essentially identical are conveniently used to make the fluid connection, rather than requiring specific male and female couplings that are different from each other. In some embodiments, such genderless couplings can have different terminations or internal components (e.g., one can include an internal valve while the other does not).

Fifth, some embodiments of the fluid coupling devices provide an improved aseptic connection capability that may optionally reduce or eliminate the need for sterile rooms or sterile benchtop environments in some cases. As such, these embodiments of the fluid coupling devices described herein may facilitate efficient and cost-effective operations or uses that would otherwise be high-cost or even cost prohibitive in some traditional settings that required the connection of particular fluid couplings in a sterile room or within a sterile flow-hood to prevent biological contamination.

Sixth, some embodiments of the fluid coupling devices provided herein are advantageously designed with a robust latching system. That is, when the two of the fluid coupling devices (or a fluid coupling device and another fluid-handling component) are operably connected with each other, they are also mechanically latched or locked together in a robust manner.

Seventh, in some embodiments when two of the fluid coupling devices (or a fluid coupling device and another fluid-handling component) are operably connected with each other, they cannot be separated. Accordingly, in some cases the potential for adverse effects such as fluid spills and environmental or process contamination are prevented or mitigated.

Eighth, some embodiments do not have springs in the fluid flow path and hence a smooth, unobstructed fluid flow path is provided by the fluid coupling devices.

In the context of this disclosure, the term "fluid" also includes gases, liquids, vapors, steam, mists, gels, semi-solids, powders, and the like, without limitation.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION OF ILLUSTRATIVE EMBODIMENTS

This document describes fluid coupling devices for fluid systems and methods of using the fluid coupling devices. For example, some embodiments described in this document are fluid couplings that can be used to provide a sterile fluid flow path connection for the delivery of therapeutic agents, or ingredients thereof, and other purposes. In some embodiments, the fluid coupling devices are used singularly as a normally-closed valve that can be used for sterile or non-sterile scenarios.

Figure 1:
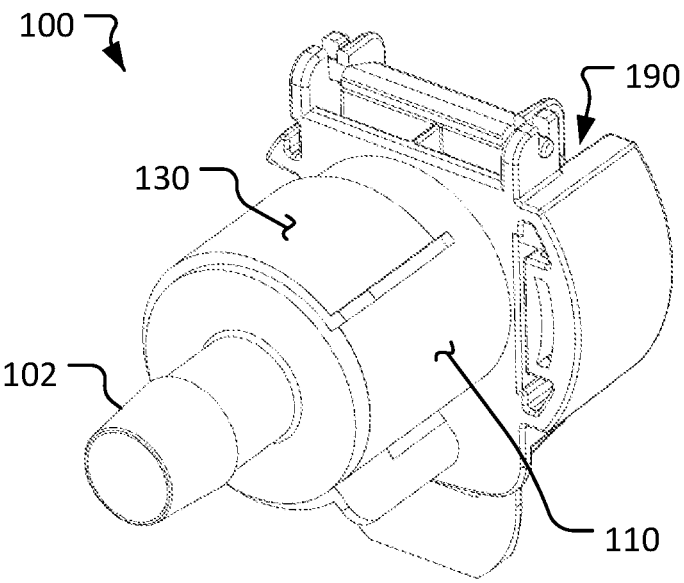
FIG. 1 is a perspective view of an example fluid coupling device, in accordance with some embodiments provided herein.
Figure 2:
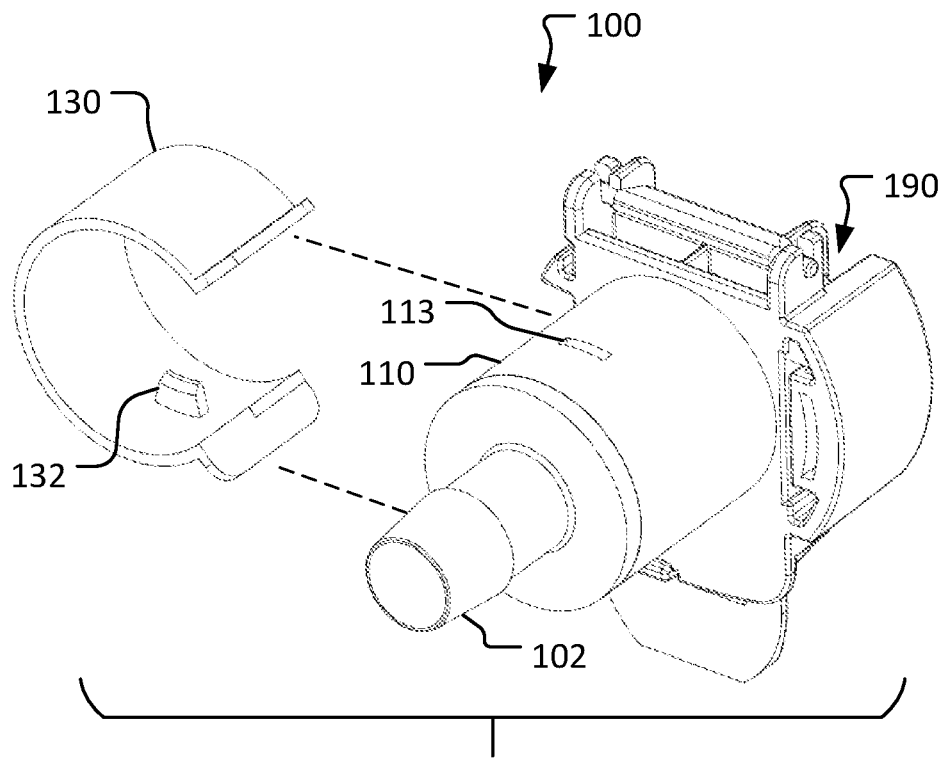
FIG. 2 is an exploded perspective view of the fluid coupling device of FIG. 1.
Figure 3:
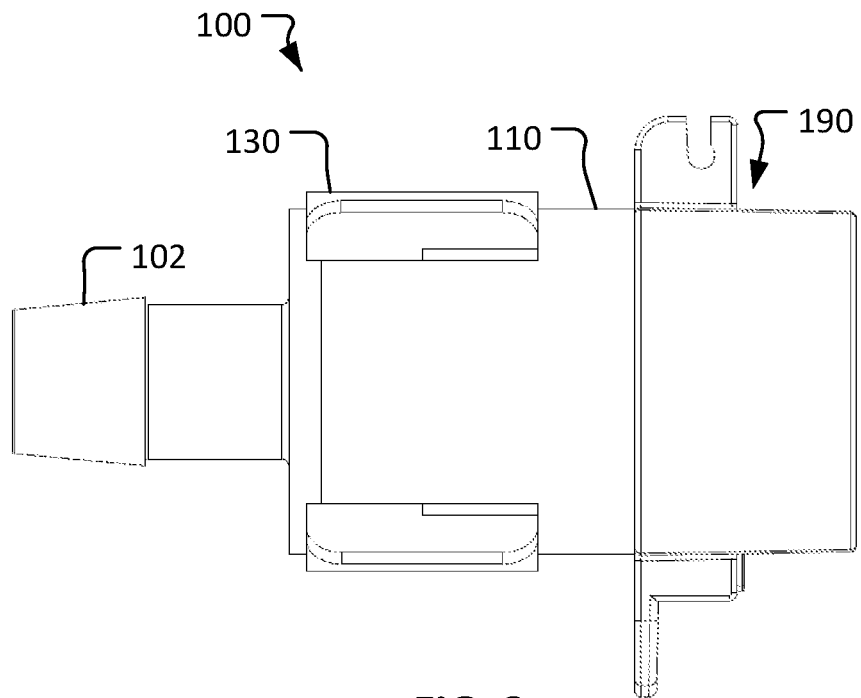
FIG. 3 is a side view of the fluid coupling device of FIG. 1.

FIGS. 1-3 illustrate an example fluid coupling device 100 (or "fluid coupling 100," or simply "coupling 100"). The coupling 100, broadly speaking, includes a housing 110 (or "main body 110") that includes a termination 102 extending therefrom, a removable member 130 that is a sleeve 130 in the depicted embodiment, and an optional connection structure 190. The connection structure 190 is on an opposite end of the housing 110 in comparison to the termination 102.

In some embodiments, the fluid coupling 100 can be configured as a "sterile" or "aseptic" coupling, meaning that the fluid coupling 100 can be coupled to another fluid-handling component in a manner that establishes a sterile fluid flow path there between. In some embodiments, the fluid coupling 100 is provided to a user as a sterilized coupling 100, or is configured to be sterilized (e.g., by gamma radiation and/or autoclave sterilization or other methods).

As described further below, the optional connection structure 190 is configured to facilitate the joining or coupling of the coupling 100 to another fluid-handling component such as, but not limited to, another coupling 100. In the depicted example embodiment, the connection structure 190 configures the coupling 100 to be a genderless coupling. Such a genderless coupling 100 is configured to allow two essentially identical couplings 100 (except perhaps for potential differences in features such as the type of termination 102, etc.) to be coupled together. Said another way, a genderless coupling (such as the example coupling 100) does not have a distinct male coupling and/or female coupling.

While the depicted termination 102 is a barbed connection, the termination 102 can be configured in any desired manner (e.g., as a luer fitting, a threaded connection, a sanitary fitting, a compression fitting, a "T-fitting," a "Y-fitting," a manifold, an elbow, any type of adapter or connector, etc., without limitation). The termination 102 defines a lumen through which the flow path of the coupling 100 extends. For example, the lumen of the termination 102 provides a portion of the fluid flow path of the fluid coupling 100 when two fluid couplings 100 are fully coupled together (as described further below).

The materials from which one or more of the components of the fluid coupling 100 are made of include thermoplastics. In particular embodiments, the materials from which the components of the fluid coupling 100 are made of are thermoplastics, such as, but not limited to, acetal, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, and the like, and combinations thereof. In some embodiments, the thermoplastics can include one or more fillers such as, but not limited to, glass fiber, glass bead, carbon fiber, talc, etc.

In some embodiments, the materials from which one or more of the components of the fluid coupling 100 are made of include metals such as, but not limited to stainless steel, brass, aluminum, plated steel, zinc, and the like. In particular embodiments, the fluid coupling 100 is metallic-free.

In certain embodiments, the seal members and sealing portions included in the coupling 100 can be made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like. The cross-sectional shapes of the seals can be circular, D-shaped, X-shaped, square, rectangular, U-shaped, multi-lobed, L-shaped, V-shaped, hourglass shaped, and the like, without limitation.

The sleeve 130 is removably coupled to the housing 110. As described further below, while the sleeve 130 is coupled to the housing 110 as shown in FIGS. 1 and 3, a valve member within the housing 110 is restrained in a first position. Then, when the sleeve 130 is removed from the housing 110 as shown in FIG. 2, the valve member within the housing 110 moves to a second position. While the sleeve 130 is included in the depicted embodiment as the removable member 130, other embodiments within the scope of this disclosure include other types of a removable member 130. For example, in some embodiments the removable member 130 is a pin, a tear-away member, a thin plate, and the like.

Figure 4:
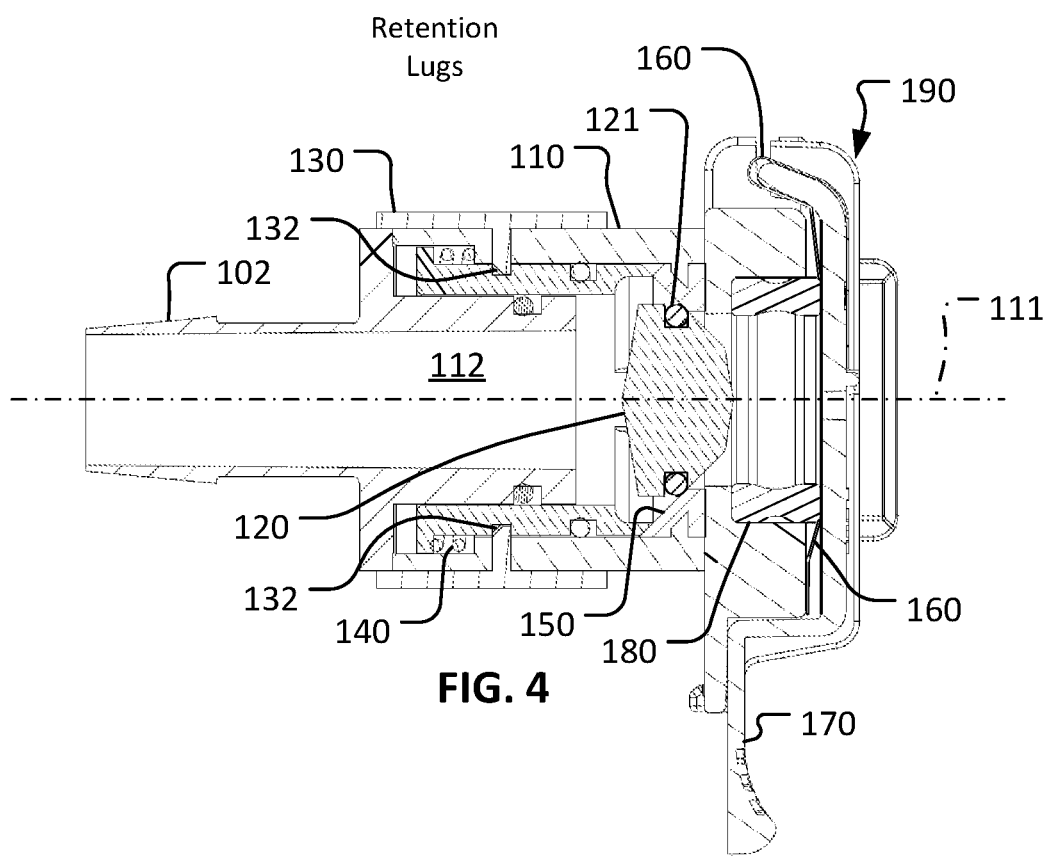
FIG. 4 is a longitudinal cross-sectional view of the fluid coupling device of FIG. 1.

Referring also to FIG. 4, the housing 110 defines a longitudinal central axis 111 extending between the termination 102 and the connection structure 190.

The housing 110 defines an internal space 112. In this cross-sectional view, additional components of the coupling 100 that are within the internal space 112 are visible. For example, the coupling 100 includes a valve member 120 (see also FIGS. 5 and 6), an optional biasing member (e.g., one or more springs 140), and a valve seat 150. The valve member 120 is movable, within the internal space 112, along the longitudinal central axis 111 between its first and second positions.

In the depicted arrangement, the valve member 120 is in a first, closed position. The depicted first position is called a closed position because the valve member 120 is abutted against the valve seat 150 to provide a fluid seal between the valve member 120 and the valve seat 150. Accordingly, there is no fluid flow path that is open through the coupling 100 while the valve member 120 is in its first, closed position.

Figure 5:
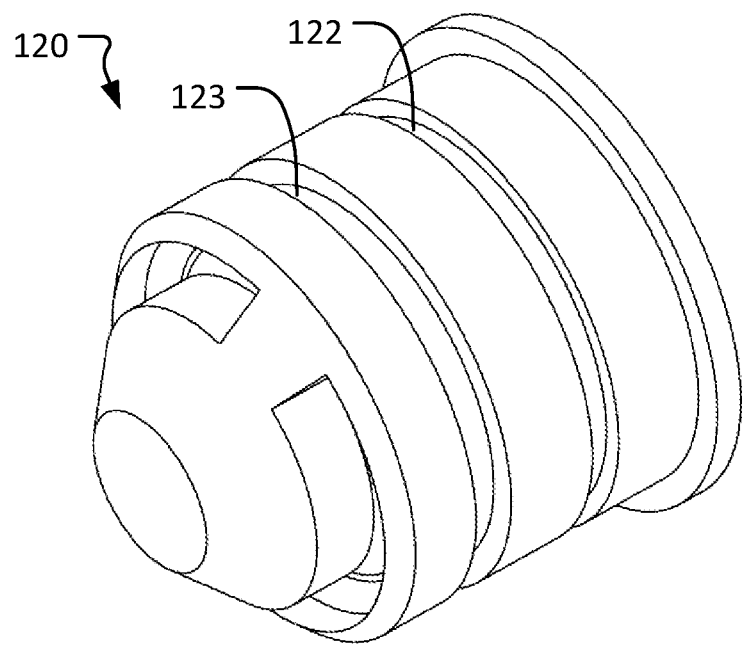
FIG. 5 is a perspective view of an example valve member of the fluid coupling device of FIG. 1.
Figure 6:
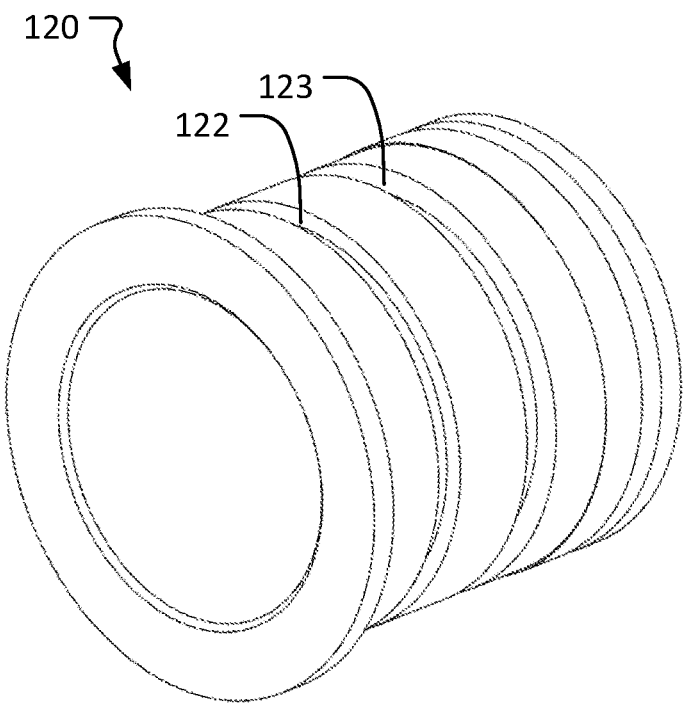
FIG. 6 is another perspective view of the valve member of FIG. 5.

In some embodiments, the valve seat 150 is a resilient elastomeric seal material that is overmolded on the housing 110 to provide a liquid-tight seal between the valve member 120 and the valve seat 150 while the valve member 120 is in its first, closed position. In some embodiments, the valve seat 150 is attached to the housing 110 in another manner, such as by using an adhesive, ultrasonic welding, press-fitting, and the like. Alternatively or additionally, in some embodiments such as the depicted embodiment, the valve member 120 includes an annular seal member 121 that is seated in an annular recess 123 (FIGS. 5 and 6). The annular seal member 121 contacts the valve seat 150 to provide a liquid-tight seal between the valve member 120 and the valve seat 150 while the valve member 120 is in its first, closed position. In some embodiments, the valve seat 150 is an elastomeric seal material. Alternatively, in some embodiments the valve seat 150 is made of the same rigid material as the housing 110, and can be integrally made with the housing 110. In such a case, the valve member 120 including the elastomeric annular seal member 121 can seal against the valve seat 150 that is made of the same rigid material as the other portions of the housing 110.

The optional spring 140 is arranged between the housing 110 and the valve member 120. More particularly, in the depicted arrangement the spring 140 is positioned to bias the valve member 120 to move away from the depicted first, closed position. However, in the depicted arrangement the valve member 120 is detained in the first, closed position by the sleeve 130 (as described further below).

Figure 8:
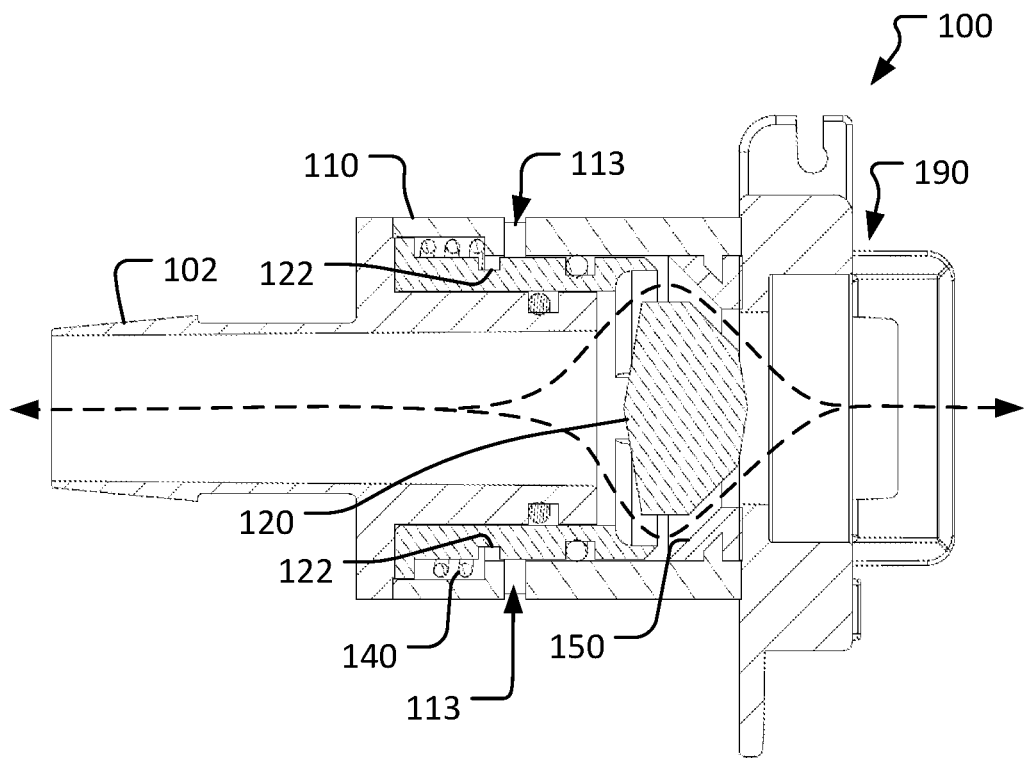
FIG. 8 is a longitudinal cross-sectional view of the fluid coupling device of FIG. 7.

In some embodiments, the spring 140 is made of a metallic material (e.g., spring steel, stainless steel such as 316L, piano/music wire, beryllium copper, titanium, and the like). In some embodiments, the spring 140 can be made of a polymeric, thermoset, or elastomeric material (e.g., PEEK, PPSU, PSU, etc.) and could include fillers (glass fiber, carbon fiber, etc.). In the depicted embodiment, the spring 140 is not in the fluid flow path (e.g., as illustrated in FIG. 8).

In the depicted embodiment, the sleeve 130 has a C-shaped cross-section and surrounds the housing 110 by greater than 180° and less than 360°. The sleeve 130 is configured to flex to allow removal of the sleeve 130 from being coupled to the housing 110.

The sleeve 130 includes one or more projections 132 that extend radially inward from the inner wall of the sleeve 130. While the sleeve 130 is coupled to the housing 110, the one or more projections 132 extend through one or more corresponding openings 113 defined by the housing 110. The one or more projections 132 that extend through the corresponding one or more openings 113 defined by the housing 110 also extend farther into the internal space 112, where they are seated into one or more recesses 122 (FIGS. 5 and 6) defined by the valve member 120. In the depicted embodiment, the one or more recesses 122 defined by the valve member 120 is a continuous annular recess or groove 122.

Figure 7:
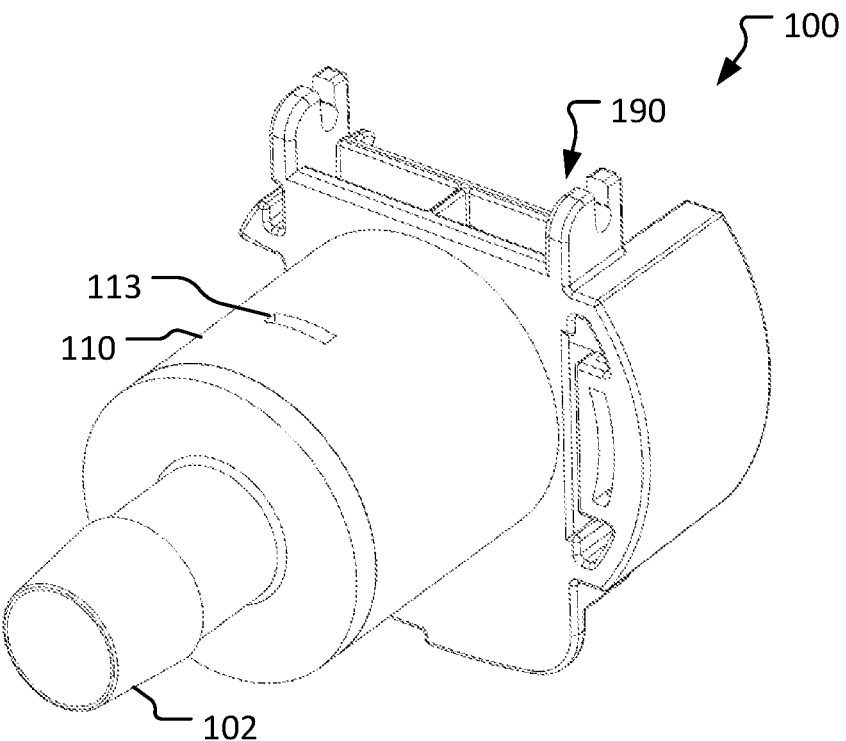
FIG. 7 is a perspective view of the fluid coupling device of FIG. 1 with its removable sleeve removed.

Because, as in the depicted arrangement, the one or more projections 132 are seated in the more recesses 122 defined by the valve member 120, the valve member 120 is mechanically detained or latched in the first position. However, when the sleeve 130 is uncoupled from the housing 110, the one or more projections 132 are no longer engaged in the more recesses 122 defined by the valve member 120 (or in the housing openings 113) and the force from the spring 140 will drive the valve member 120 away from its first, closed position. Said another way, the valve member 120 will move to its second, open position when the sleeve 130 is uncoupled from the housing 110. Accordingly, a fluid flow path will become opened through the coupling 100 when the sleeve 130 is uncoupled from the housing 110. This is depicted in FIGS. 7 and 8 (including the open fluid flow path that is illustrated by the broken lines in FIG. 8).

In the depicted embodiment, the one or more projections 132 consists of two projections 132. While not required in all embodiments that include two projections 132, in the depicted embodiment the two projections 132 are arranged 180° opposite of each other on the sleeve 130. In some embodiments, the one or more projections 132 consists of one projection, three projections, four projections, or more than four projections. In some embodiments, there is a single projection 132 that is 90 degrees between the depicted projections 132. In such a case, and when the sleeve 130 is oval the clearances are right, then deforming the sleeve 130 will disengage projection 132 without having to remove the sleeve 130 from the housing 110.

In some embodiments, as an alternative to the flexible sleeve 130 with the C-shaped cross-section as shown, in some embodiments the sleeve 130 can be fully 360° around the housing 110 and configured to be ruptured or torn (or deformed) in order to remove the sleeve 130 from being coupled to the housing 110.

Figure 9:
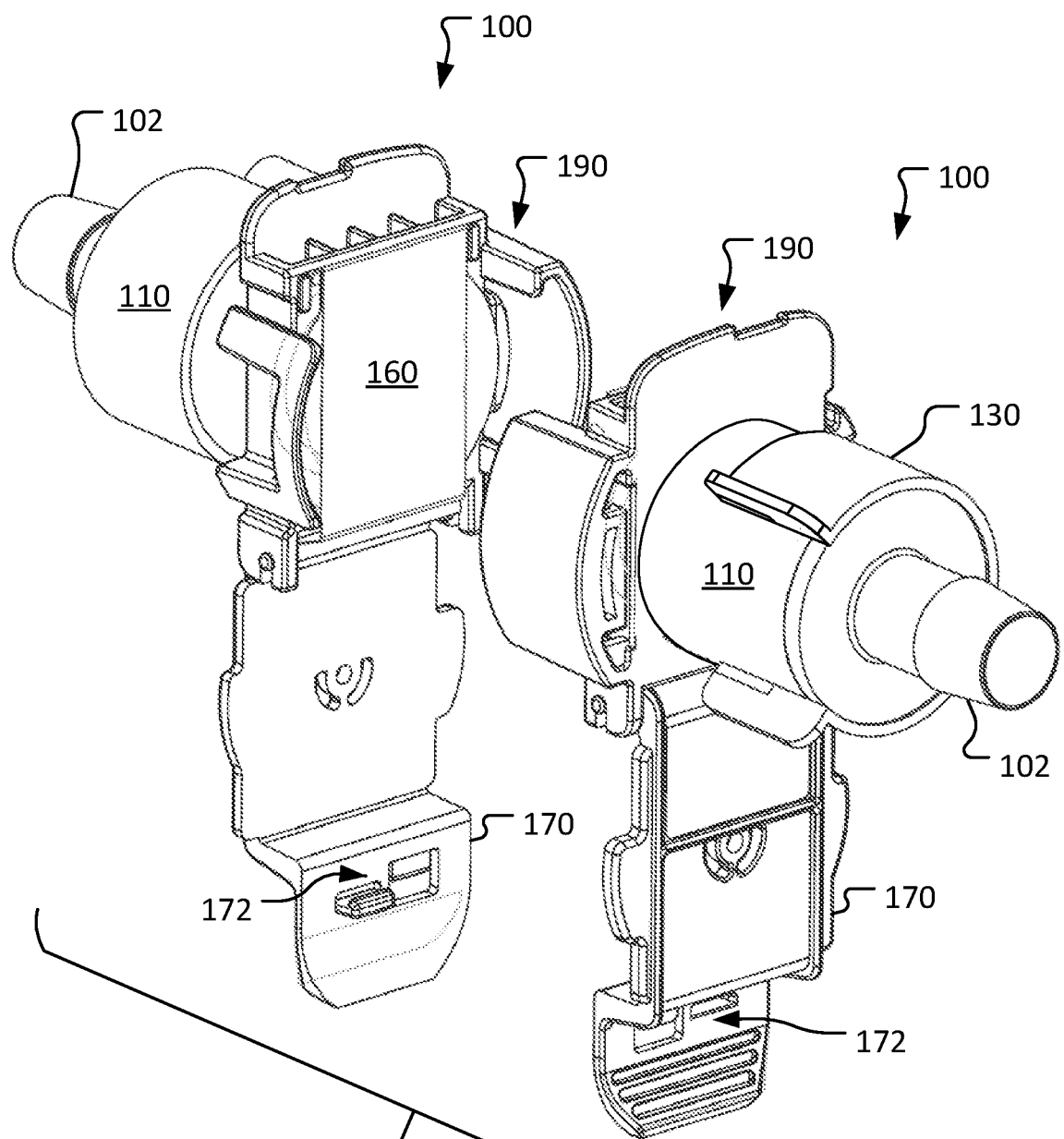
FIG. 9 is a perspective view of two of the fluid coupling devices of FIG. 1 in alignment in preparation for coupling together.

Still referring to FIG. 4 and now also to FIG. 9, the coupling 100 optionally includes a membrane 160, a handle 170, a seal member 180, and the connection structure 190. However, it should be understood that these components of the coupling 100 are merely optional examples of components and structures that can be used in conjunction with the coupling 100. Many other variations and components can also be used with the coupling 100.

In some embodiments, such as the depicted embodiment, the seal member 180 has an hourglass cross-sectional shape. In some such embodiments of the seal member 180, the seal member 180 has a waist portion in the middle of two thicker end portions (e.g., see FIG. 4). The radial thickness of the waist portion is thinner than the two end portions of the seal member 180. In some such embodiments, the outer and inner surfaces of the waist portion are arcuate. In such a case, the center of the arc that defines the outer surface of the waist portion is located in an opposite direction in comparison to the center of the arc that defines the internal surface of the waist portion. In some such embodiments, the radii of the arc of the outer surface and the arc of the internal surface are unequal. In some such embodiments, the radii of the arc of the outer surface and the arc of the internal surface are equal.

The seal member 180 is positioned within a cylindrical recess (or counter bore) that is defined by the front face of the housing 110. The width of the seal member 180 (taken directionally along the longitudinal axis 111) is slightly larger than the depth of the cylindrical recess. Accordingly, an end portion of the seal member 180 extends outward, away from the front face of the housing 110 and toward the removable membrane 160. Put another way, the seal member 180 stands proud of the front face of the housing 110.

The membrane 160 is a thin, flexible member. The membrane 160 can be made of materials such as, but not limited to, polyethersulfone (PES), non-woven polyethylene such as Tyvek®, a PES and polyester laminate, expanded polytetrafluoroethylene (ePTFE), metallic foil, and the like, and combinations thereof. In some embodiments, the membrane 160 can include an adhesive on all, or just portions, of the surface of the membrane 160. In some embodiments, membrane 160 is hydrophobic and breathable. In particular embodiments, the pore size of the membrane 160 is such that microorganisms larger than 0.2 microns are filtered out.

The membrane 160 is removably attached to the front face of the housing 110. The membrane 160 can be removably attached to the front face of the housing 110 by being bonded (e.g., heat welding, ultrasonic welding, etc.) to the front face such that the membrane 160 is at least circularly bonded around the cylindrical recess of the housing 110 to cover the seal member 180. Any suitable bonding technique to removably couple the membrane 160 to the front face surface of the housing 110 can be used, such as using adhesive. The membrane 160 maintains the sterility and/or cleanliness of the seal member 180 and adjacent portions of the internal space 112 (e.g., with the termination 102 being capped or coupled to another sterile component).

The membrane 160 is folded over on itself. Accordingly, as described further below, when the membrane 160 is removed from its attachment to the front face of the housing 110, the membrane's fold will progress in the direction of the pulling, and the membrane 160 will effectively roll off (or peel off) the front face of the housing 110 to reveal the seal member 180.

The handle 170 is attached to the membrane 160, on an opposite end of the membrane 160 in comparison to the portion that is attached to the front face of the housing 110. The handle 170 provides a grasping member to be used when a user chooses to detach the membrane 160 from the front face of the housing 110, as described further below.

The handle 170 is releasably coupleable to the housing 110 in multiple arrangements. In a first arrangement as depicted in FIG. 4, the handle 170 is latched to the housing 110 in a position in which the handle 170 functions as a cover that covers and protects the portion of the membrane 160 that is removably attached to the front face surface of the housing 110. In a second arrangement as depicted in FIG. 9, the handle 170 has been pivoted in relation to the housing 110 (in comparison to the arrangement of FIG. 4) such that the portion of the membrane 160 that is removably attached to the front face surface of the housing 110 is uncovered, while the handle 170 is still coupled to the housing 110.

As depicted in FIG. 9 (and the subsequent figures), two of the couplings 100 can be coupled together. The connection structure 190 is designed to facilitate the two couplings 100 (which are identical in this example) to be coupled to each other, and to then detain the two couplings 100 in the coupled arrangement (e.g., by snapping together). Accordingly, the coupling 100 can be termed to be a genderless coupling. In some embodiments, the connection structure 190 is designed to prevent the couplings 100 from being uncoupled from each other after two of the couplings 100 have been coupled to each other.

In FIG. 9, the two couplings 100 are being prepared for coupling to each other. That is, the handles 170 have been pivoted open to their second arrangement in which the portions of the membrane 160 that are removably attached to the front face surface of the housing 110 are exposed. The two couplings 100 still have their sleeves 130 coupled to the housings 110. Accordingly, the internal valve members 120 are still detained in their first position (which, in the depicted embodiment, is a closed position that blocks fluid flow through the couplings 100). The longitudinal axes 111 of the two couplings 100 are aligned with each other and the connection structures 190 are aligned in preparation for engagement. Then, the two couplings 100 can be moved toward each other so that the connection structures 190 mate together.

Figure 10:
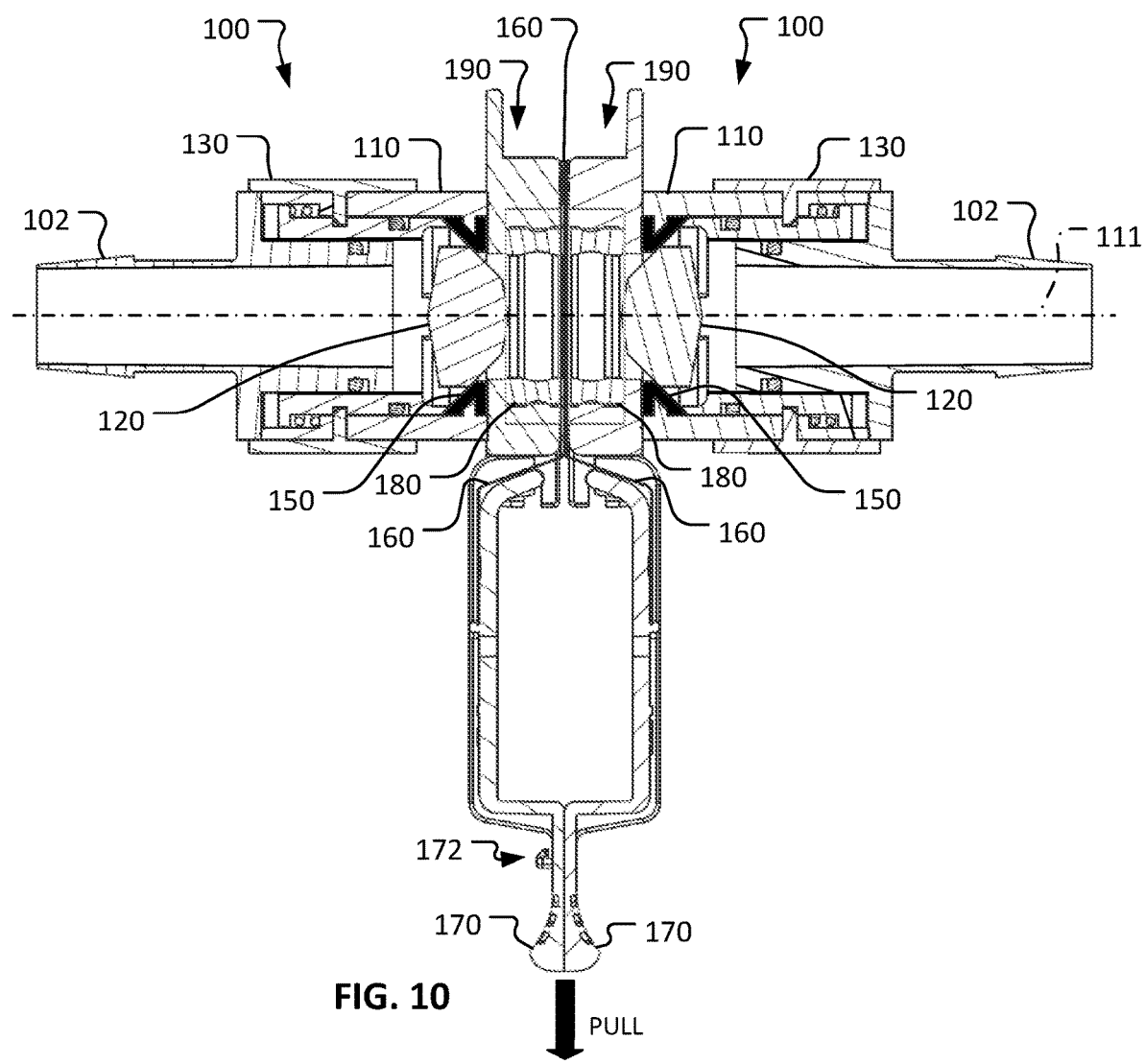
FIG. 10 is a longitudinal cross-sectional view of two fluid coupling devices of FIG. 1 in a pre-coupled arrangement.

FIG. 10 shows a longitudinal cross-sectional view of the two couplings 100 that have been coupled to each other in a "pre-coupled configuration." In the depicted pre-coupled configuration, the two couplings 100 are mechanically coupled to each other via the connection structures 190, but the membranes 160 are still attached to the front face surfaces of the housings 110. To put it simply, the membranes 160 are sandwiched between the seal members 180. In fact, because of the folds in the membranes 160, there are actually four (4) layers of the material of the membranes 160 that are sandwiched between the seal members 180.

The handles 170 are aligned with each other (approximately in a reverse mirrored arrangement). In some embodiments, the handles 170 include latching structures 172 that allow the handles 170 to be snapped together in the mirrored arrangement, and thereby latched to each other so that they can be conveniently handled as a single entity/unit. In this pre-coupled configuration, the sleeves 130 are still coupled to the housings 110. Accordingly, the internal valve members 120 are still detained in their first position (which, in the depicted embodiment, is a closed position that blocks fluid flow through the couplings 100). In some embodiments, the couplings 100 include an interlock feature that prevents the sleeves 130 from be removed until the membranes 160 have been detached from the couplings 100.

The next step in the process of fully coupling the two couplings 100 together is to remove the membranes 160 that are attached to the front face surfaces of the housings 110 (and that are between the seal members 180). This can be done by pulling on the handles 170 in a direction that is transverse to the longitudinal axes 111 (as indicated by the arrow shown in FIG. 10). Due to the folds in the membranes 160, as the handles 170 and attached membranes 160 are pulled, the membranes 160 will effectively roll off the faces of the housings 110, and the seal members 180 will then become abutted against each other. This rolling of the membranes 160 ensures that no potentially contaminated portions of the membranes 160 make contact with the seal members 180 as the membranes 160 are removed.

Figure 11:
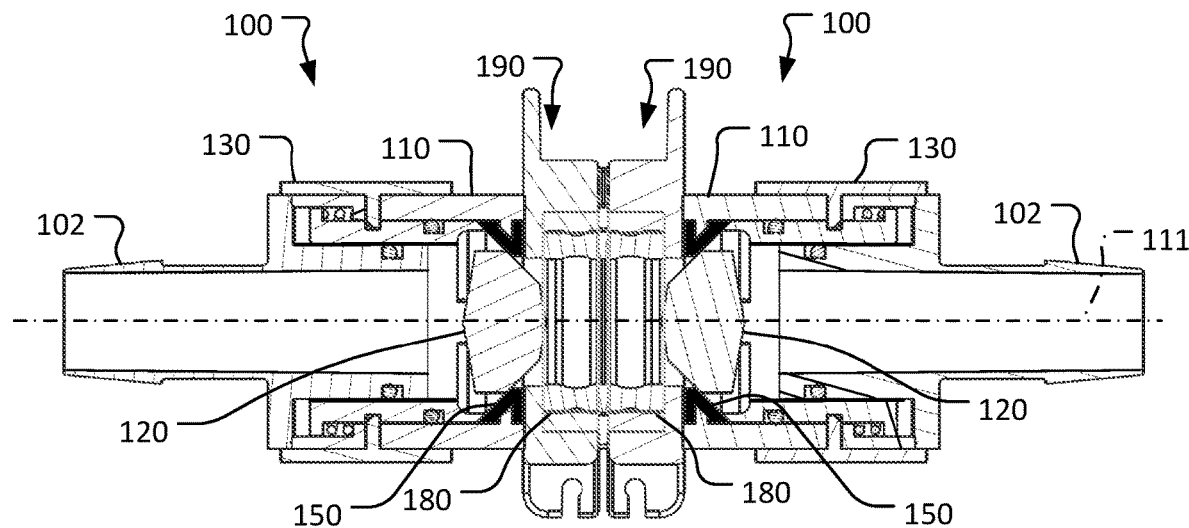
FIG. 11 is a longitudinal cross-sectional view of two fluid coupling devices of FIG. 1 in a coupled arrangement and prior to the opening of the fluid flow path.

FIG. 11 shows a longitudinal cross-sectional view of the two couplings 100 after the membranes 160 have been stripped away. The front faces of the seal members 180 are now abutting, and are firmly compressed against each other by the on-going longitudinal compressive forces provided by the latching mechanisms of the connection structures 190. In the depicted arrangement, the sleeves 130 are still coupled to the housings 110. Accordingly, the internal valve members 120 are still detained in their first position (which, in the depicted embodiment, is a closed position that blocks fluid flow through the couplings 100). The next step in the process of fully coupling the two couplings 100 together is to remove the removable members 130 (that is, to remove the sleeves 130, in the depicted embodiment).

Figure 12:
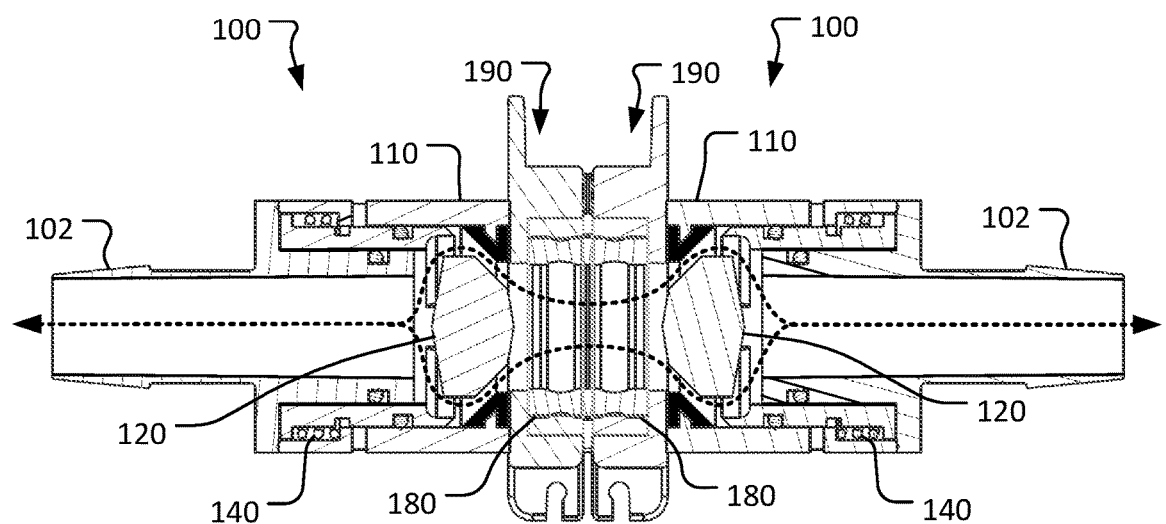
FIG. 12 is a longitudinal cross-sectional view of two fluid coupling devices of FIG. 1 in a coupled arrangement with an open fluid flow path therethrough.

FIG. 12 shows a longitudinal cross-sectional view of the two couplings 100 after the sleeves 130 have been uncoupled from the housings 110. Because the sleeves 130 were detaining the valve members 120 in the their first position, with the sleeves 130 now removed the forces from the springs 140 can act on the valve members 120 to move the valve members 120 to their second position (which, in the depicted embodiment, is an open position that creates an open fluid flow path through the couplings 100, as indicated by the dashed lines). This is the final, operational configuration of the two couplings 100 as described herein. Accordingly, fluid can be transferred through the couplings 100 from one container to another, one tube to another, or (more generally speaking) from one fluid-handling component of any type to another.

While in the depicted embodiment, each of the couplings 100 has a valve member 120, in some cases only one of the couplings 100 of a pair of couplings 100 has a valve member 120. This can be referred to as a single-sided shutoff.

While the embodiments of the couplings 100 described herein are normally closed fluid couplings, in some embodiments the fluid coupling devices can be configured to be normally open. That is, when the sleeves 130 are removed, the valve members 120 will move from a first position (which is an open position) to a second position (which is a closed position).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described herein should not be understood as requiring such separation in all embodiments, and it should be understood that the described components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of creating an aseptic fluid flow path, the method comprising:
    coupling a fluid coupling device to a second fluid-handling component, wherein the fluid coupling device comprises:
        a housing defining an internal space;
        a removable membrane;
        a valve member movably disposed within the internal space, wherein the valve member isolates fluid in the internal space from reaching the membrane when the valve member is in a closed position; and
        a member removably coupled to the housing and in engagement with the valve member to thereby retain the valve member in the closed position;
    after the coupling of the fluid coupling device to the second fluid-handling component, removing the membrane from between the fluid coupling device and the second fluid-handling component;
    after the removing the membrane, removing the member from the housing.

2. The method of claim 1, wherein the removing the member from the housing allows the fluid in the internal space to flow into the second fluid-handling component.

3. The method of claim 1, wherein the valve member moves from the closed position to an open position in response to the removing the member.

4. The method of claim 1, wherein the member includes one or more projections.

5. The method of claim 4, wherein the one or more projections extend through one or more openings defined by the housing.

6. The method of claim 1, wherein the second fluid-handling component is identical or essentially identical to the fluid coupling device.

7. The method of claim 6, wherein the removing the membrane includes removing a membrane of the second fluid-handling component.

8. The method of claim 1, wherein removing the member from the housing comprises flexing the member.

9. The method of claim 1, wherein removing the member from the housing comprises tearing the member.

10. The method of claim 1, wherein the fluid coupling device further comprises a spring disposed within the internal space, wherein force from the spring exerted on the valve member moves the valve member from the closed position to an open position in response to the removing the member.

11. The method of claim 1, wherein the spring is outside of a fluid flow path defined by the fluid coupling device.

12. The method of claim 1, wherein the membrane includes a portion removably attached to a front face surface of the housing and covering an end portion of a seal member that projects longitudinally beyond the front face surface.

13. The method of claim 12, further comprising a handle attached to the membrane, and wherein the handle is releasably coupleable to the housing.

14. The method of claim 13, wherein, while the handle is coupled to the housing, the handle covers the portion of the membrane that is removably attached to the front face surface of the housing.

15. A method of creating an aseptic fluid flow path, the method comprising:
    coupling a fluid coupling device to a second fluid-handling component, wherein the fluid coupling device comprises:
        a housing defining an internal space;
        a valve member movably disposed within the internal space in a closed position in which the valve member isolates fluid in a first portion of the internal space; and
        a member removably coupled to the housing and in engagement with the valve member to thereby retain the valve member in the closed position; and
    after the coupling of the fluid coupling device to the second fluid-handling component, removing the member from the housing.

16. The method of claim 15, further comprising, after the coupling of the fluid coupling device to the second fluid-handling component but prior to the removing of the member from the housing, removing a membrane from between the fluid coupling device and the second fluid-handling component.

17. The method of claim 15, wherein the removing the member from the housing allows the fluid in the first portion of the internal space to flow into the second fluid-handling component.

18. The method of claim 15, wherein the valve member moves from the closed position to an open position in response to the removing the member.

19. The method of claim 15, wherein the second fluid-handling component is identical or essentially identical to the fluid coupling device.

20. The method of claim 19, further comprising, after the coupling of the fluid coupling device to the second fluid-handling component but prior to the removing of the member from the housing, removing two separate membranes from between the fluid coupling device and the second fluid-handling component.

* * * * *